United States Patent [19]

Youssef

[11] 4,299,921
[45] Nov. 10, 1981

[54] PROLONGED INCUBATION MICROBIOLOGICAL APPARATUS AND FILTER GASKETS THEREOF

[76] Inventor: Kamal A. Youssef, P.O. Box 6548, W. Palm Beach, Fla. 33405

[21] Appl. No.: 180,031

[22] Filed: Aug. 21, 1980

Related U.S. Application Data

[63] Continuation-in-part of Ser. No. 25,461, Mar. 30, 1979, abandoned.

[51] Int. Cl.³ .............................................. C12M 1/22
[52] U.S. Cl. .................................... 435/298; 215/348; 215/349; 277/227; 277/228; 277/233
[58] Field of Search ............... 435/298, 297, 296, 299, 435/300, 301, 287, 801; 277/227, 228, 229, 230, 233, DIG. 6; 215/348, 349, 261; 220/373, 378

[56] References Cited

U.S. PATENT DOCUMENTS

| | | | |
|---|---|---|---|
| 1,513,360 | 10/1924 | Ablahadian | 435/296 X |
| 2,533,088 | 12/1950 | Brewer et al. | 435/298 X |
| 3,055,808 | 9/1962 | Henderson | 435/298 |
| 3,158,553 | 11/1964 | Carski | 435/298 |
| 3,184,395 | 5/1965 | Brewer | 435/299 X |
| 3,246,767 | 4/1966 | Pall et al. | 210/505 |
| 3,248,302 | 4/1966 | Mackin | 435/298 |
| 3,326,401 | 6/1967 | De Long | 435/311 X |
| 3,520,416 | 7/1970 | Keedwell | 210/490 |
| 3,896,959 | 7/1975 | Roy | 215/348 X |
| 3,976,217 | 8/1976 | Dukess | 215/348 X |
| 4,009,285 | 2/1977 | Spooner | 435/296 X |
| 4,121,728 | 10/1978 | Tagalakis et al. | 215/348 X |

*Primary Examiner*—Robert J. Warden
*Attorney, Agent, or Firm*—Albert F. Kronman

[57]  ABSTRACT

Apparatus for the culture of aerobic, anaerobic organisms and tissue which is formed of two sections, one fitting with the other as a cover and has a lubricated open cell foam filter gasket having on one side a microporous membrane and on the other, a non-porous layer. The gasket is fitted to the cover section or onto the rim of the container section and minimizes the chances of contamination from the ambient or otherwise gaseous atmosphere of incubation of the culture or biological material contained therein when closed and/or in use.

1 Claim, 4 Drawing Figures

PROLONGED INCUBATION MICROBIOLOGICAL APPARATUS AND FILTER GASKETS THEREOF

CROSS-REFERENCE TO CO-PENDING APPLICATION

This application is a continuation-in-part of my previous application Ser. No. 25,461, filed Mar. 30, 1979, and now abandoned.

FIELD OF THE INVENTION

This invention concerns apparatus of the Petri dish type and a contamination-proof, prolonged incubation sealing gasket therefore.

BACKGROUND OF THE INVENTION

One of the shortcomings of the Petri dish is that there is no control over the biological or physical characteristics of the air or gas that gets into or out of the Petri dish. Ventilation in a Petri dish is often a desirable feature and is presently provided by the "beading" of the rim of the container section if the dish is made of glass and by the presence of "ridges" (usually three) either on the cover at its circumference on the inside or on the rim of container section. These "ridges" or "protrusions" will ensure the presence of a space or a physical gap between the container section and the cover. This gap, however, is big enough to allow not only dust and suspended particulate matter (occasionally) dangerous material e.g. spores of pathogenic fungi to get in (or out) of the plate but also relatively large insects as well e.g. flies and even mites and small roaches to creep freely in and out.

The second disadvantage of this structural deficiency of Petri dishes is that culture media and other relatively volatile constituents dry or dessicate fairly rapidly. Hence, culture of micro-organisms which grow slowly such as Mycobacteria e.g. T.B. and Fungi e.g. Dermatophytes and Dimorphic Fungi are endangered by the rapidly decreasing water content of the culture medium i.e. the medium dries out.

It has been difficult to store cultures on agar plates except for a limited time and the convenience such stored cultures may offer is thereby lost. The same is true for unused media i.e. they cannot be stored for a long time. It is quite evident, then, that with presently known devices, there can be little or practically no control over the gas entering or that may be coming out of a Petri dish or its contents.

There is a definite flow of air in and out of a Petri dish culture as explained by the simple law of gas expansion and shrinkage under varying temperature conditions. Culture media are usually stored at low refrigerator temperatures and have to be warmed when cultures are made. This inevitably entails the expansion of air from inside the plate to the outside. When the plates are removed from the warm temperature of the incubator to be examined at cooler room temperature, the air in the plate has to shrink inviting air from outside into the plate. All these air "movements" happen on account of change in conditions of a purely physical nature (i.e. temperature changes). On the other hand, cultures of microorganisms many of which very actively absorb and/or produce gases generate a relentless fairly strong (sometimes with great force e.g. stormy fermentation by *Clostridium welchii*) flow of gases in and out of the culture plates. For example, oxygen goes in and carbon dioxide and sometimes hydrogen sulfide go out.

DESCRIPTION OF THE PRIOR ART

The prior art to which this invention relates consists of the following U.S. Pat. Nos. 3,158,553; 3,184,395; 1,513,360 and 3,326,401. The first of these describes a Petri dish fitted with a pressure-sensitive adhesive which releasably attaches the cover to the dish and hermetically seals the juncture between the dish and its cover, being removable with the cover from the dish. U.S. Pat. No. 3,184,395, provides and envelope for aerobic culturing made of two layers of flexible, thermoplastic material having a sealing connection along the edges thereof and a plurality of heat seal partitions extending inwardly from opposite sides of the envelope, both of the layers being impervious to the culture media and at least one of the layers being pervious to air. U.S. Pat. No. 1,513,360 describes a closure wherein a test tube is provided with a circumferential groove toward the top thereof with cotton disposed in the groove and compressed by a cap removably disposed over the open end of the tube and over the groove. U.S. Pat. No. 3,326,401 shows a closure cap with a top having an opening receiving a plug supported intermediate a gasket abutting the end wall and the top of the container. Thus none of the prior art structures known to me suggests a micronized filter gasket of the present type or its equivalent.

OBJECTS AND SUMMARY OF THE INVENTION

It is an object of this invention to provide apparatus in different models to suit different purposes according to the material from which they are made.

Another object of this invention is to provide the plates with suitable filters to allow biological and physical control over the gases and other matter live or dead getting into or out of the plates, hence a greater control over the contents of the apparatus commonly referred to as the Petri dish.

In accomplishment of the above stated objects of the invention, there is provided a three ply lubricated filter gasket for a Petri dish, or other containing apparatus, consisting of a compressible open celled foamed plastic or fibrous paper core substrate having on one side an air-permeable but particulate-impermeable membrane or laminate and on the other side, a non-porous layer. There is also provided a containing apparatus comprising a cover and dish portion including a base having a peripheral wall and a terminal rim. The subject gasket is secured between the rim of the dish and the cover to seal the juncture between the dish and its cover. Preferably, the novel gasket extends along the downturned peripheral edge of the cover and along the upper edge of the rim. The gasket can be adhered to either the cover or the dish with a sealant material being applied between the gasket and the section to which it is not fixed.

DISCLOSURE

Figure 1:
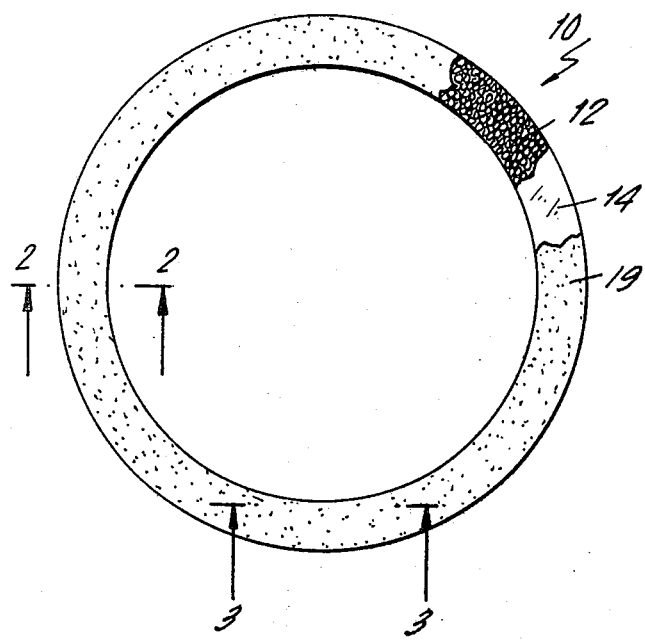
FIG. 1 is a top planar view of the gasket of the invention with parts broken away.
Figure 2:
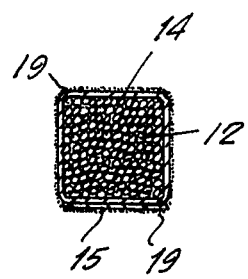
FIG. 2 is a cross-sectional view of same taken along line 2—2 of FIG. 1.
Figure 3:
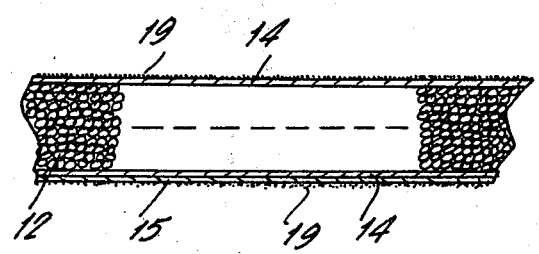
FIG. 3 is a longitudinal sectional view of same taken along line 3—3 of FIG. 1; and, FIG. 4 is a sectional view through a Petri dish assembly incorporating the gasket of the invention.

Referring now to the drawing, gasket 10 is formed of a compressible substrate core 12 such as plastic or paper which is open celled or foamed and on one side of which is secured a gas permeable but particulate and bacteria impermeable microporous membrane 14. Core 12 can be made of polyurethane foam, polyethylene foam, silicon foam, foamed cellulose, wool, silk, rayon and the like having a pore size less than 1 mm in diameter. Suitably, gasket 10 will be rectangular or rounded in cross-section and about 2 to 5 mm thick and wide.

Membrane 14 can be made from a variety of substances such as sheets made from intimately woven polyethylene fibers (such sheets are commercially available from Dupont under the name "TYVEK"). These sheets allow the passage of gases sufficiently to sustain the growth of microorganisms and cells inside the plate, but hinder bacteria and other microscopic particles, such as dust, pollen, etc. from gaining access to the inside of the plate.

The membrane 14 also cuts down on the rate of evaporation from containers protected by it since the permeation of water vapor through it is restricted to a certain degree. Membrane 14 can also be made from thin plastic sheets or films or skins with submicronic pores (0.2 micron known as absolute sterility pores) or even 0.45 microns which still is adequate to prevent contamination and allow gaseous permeation at the same time while cutting down on the rate of evaporation of water from the containers fitted with such membranes (as integral part of the filter). The membrane 14 hinders bacteria, spores or other particulate matter from gaining access into the containers once the container is sealed with a suitable sealant or lubricant as the case may be.

The membrane 14 can also be manufactured from a very wide variety of natural or synthetic materials organic and inorganic (or a blend therefrom), either with a submicronic porosity or from intimately woven fibers thereof. Such substances may include cotton (virgin or chemically treated), wool, artificial silk, nylon, Teflon, polyester, etc. Nitro-cellulose is also a suitable material for such submicronic porous material sheets. For economic reasons, "Tyvek" and Cellophane and Cellophane-plastic blends are the most practical to use and are readily available. The membranes are very thin, are measured in terms of mils rather than millimeters and vary from 6-10 mils in thickness.

The core 12 suitably is made from soft foam sheets such as polyurethane foam a few millimeters in thickness (3-5 mm) with an open cell structure.

The third layer 15 is non porous in texture and made of polyethylene, nylon, polyester, "Dacron", or "Teflon", having a thickness not exceeding 2 mils. The three elements are laminated by a process of heat-lamination and/or by the application of a glue or resin and/or wax or a polyolefin. The glue can be a simple gelatin or dextrin hardened and/or its hydrophilic property modified or rendered less hydrophilic by formaldehyde gas exposure or a 4% formalin solution. Hydrophobic (or water-proof) adhesives can also be used, including silicone and non-silicone based formulations (e.g. natural or synthetic rubber, polymers and/or esters). The width of the filter will be in the range of 2-5 millimeters or more.

The gaskets either dye-cut from the laminated sheets or fabricated in a mold in which the foam is formed "in situ" and allowed to set before the gaskets are taken out of the mold. The surface of the gasket is lubricated by a microscopic (or almost microscopic) film 19 of a silicone grease (lubricant) similar to those used in pre-lubricated condoms. A very thin film of petroleum jelly (Vaseline) or a mineral oil such as paraffin oil can also be used to ensure the sealing of the gasket.

Figure 4:
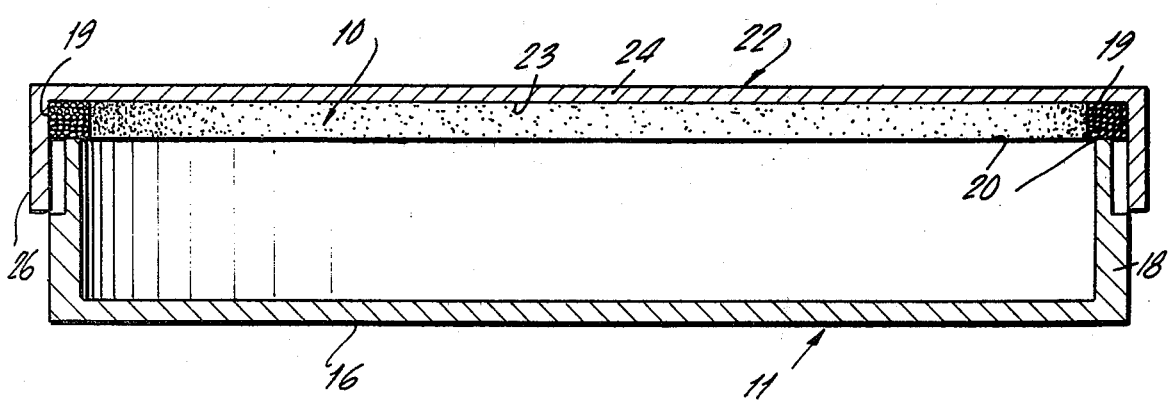

FIG. 4 shows a Petri dish 11 provided with a gasket 10. The dish can be of any shape and made of any suitable material. It includes a base 16 with a wall 18 extending upwardly therefrom. Wall 18 is formed with an upper peripheral edge 20. A cover 22 is associated with edge 20 of the dish in any suitable way for sealing the assembly. Preferably, cover 22 will have a top 24 whose inner peripheral surfaces 23 are adapted to seal with edge 20. Gasket 10 is fixed to cover 22 on the inside and the wall 26 of the cover by heat sealing or by means of an adhesive such as a silicone cement acrylic glue or a solvent used sparingly. The adhesive used need not be gas permeable. It is also possible to have the top part "cover" equipped with a circumferential "bed" on the "inside" of about 3-5 mm in width to hold mechanically "snugly fitting" the gasket which may be in the form of a ribbon instead of a dye-cut gasket and without the need for any glue or adhesive and without wasting of material in the dye-cutting process. The depth of the bed may vary to match the thickness of the gasket. Dish 1 can be manufactured in glass (with a flat brim surface "Bead-Free") or from plastic or polycarbonate in different heights 10, 15, 20, 25, 30 millimeters or higher and in different diameters e.g. 60, 90, 120, 150 millimeters, etc. to suit different purposed.

It is also possible to manufacture the dish with its base 16 divided into 2, 3, 4, sections, or more, as selected for differential diagnostic work or with a grid marking to help in different counts.

The cushioning quality of the intermediate foam layer 12 eliminates leaks, bypasses or loopholes and assures, together with the sealing action of the lubricant, that any air going into or out of the dish 11 must filter through, thus the full potential of a filter action is utilized. This gasket 10 not only eliminates microbial contamination from the ambient atmosphere but also prevents the exit or dissemination of microorganisms and their spores as well as of small insects (mites and ants, even flies and roaches).

In addition, the gasket 10 cuts down on the rate of escape of water vapor to the ambient atmosphere (or incubator atmosphere), thereby becoming an invaluable device for the prolonged incubation of cultures where drying of the culture medium jeopardizes the viability of the microorganisms, particularly, slowly-growing micro-organisms and cells such as Fungi, Mycobacteria and tissue culture. The reduced rate of water vapor escape from the dishes also prolongs the shelf life of the prepared culture media and ensures the very important (often critical) buildup and particularly the maintenance of the microscopic film of moisture on the surface of the culture medium so essential for initial critical phase of growth (the lag phase and beginning of the logarithmic phase) and guarantees that the culture medium remains moist all the way from the surface film 19 down to the bottom of the base 16 for longer periods of time. This is even more critical for the very delicate and dryness-sensitive microorganisms such as the Meningococcus, Gonorhoea germs, Cryptococcus (Meningitis Yeast)

and several other microorganisms which are extremely important medically.

As the gasket cuts down upon the rate of escape of water vapor from the dish 11, it will allow the free exchange of gases of vital importance between the inside of the dish namely, oxygen and carbon dioxide and the ambient or incubation atmosphere in the incubation chamber whichever may be the case.

It will be appreciated that modifications may be made in the illustrative embodiments of my invention within the scope of the subjoined claims. Thus the specific size, shape and configuration of the containers and dishes may be changed, any appropriate culture media may be employed and the apparatus may be used for the culturing of any microorganisms.

What is claimed is:
1. An apparatus for the culture of aerobic or anaerobic organisms or tissue, comprising a dish member having an upstanding periphal wall and a cover provided with a downturned rim fitting over at least a part of said wall; a filter gasket for sealing the juncture between said wall, said cover and said rim, comprising a compressible open-called core, a microporous air permeable and particulate impermeable membrane on one side of said core adapted to adhere to the inside of said cover and to its rim, said core having on its other side a non-porous layer adapted to adhere to the cover of said dish; said gasket having also an external, substantially microscopic lubricating film to ensure sealing engagement between said dish and said cover.

* * * * *